United States Patent [19]

Lusk et al.

[11] Patent Number: 5,278,284

[45] Date of Patent: Jan. 11, 1994

[54] PROTEIN PURIFICATION METHOD

[75] Inventors: Lance T. Lusk, Milwaukee; Henry Goldstein, Brookfield, both of Wis.

[73] Assignee: Miller Brewing Company, Milwaukee, Wis.

[21] Appl. No.: 882,793

[22] Filed: May 14, 1992

[51] Int. Cl.$^5$ .................... C07K 3/18; C07K 3/22
[52] U.S. Cl. .................... 530/305; 530/412; 530/415
[58] Field of Search .............. 530/412, 305, 415; 502/407; 426/330.4, 422; 435/183

[56] References Cited

U.S. PATENT DOCUMENTS

| | | | |
|---|---|---|---|
| 2,769,747 | 11/1956 | Sampson | 530/305 |
| 3,436,225 | 4/1969 | Raible | 99/48 |
| 3,617,301 | 11/1971 | Barby | 99/48 |
| 3,945,988 | 3/1976 | Khann et al. | 530/305 |
| 4,246,351 | 1/1981 | Miyake et al. | 435/182 |
| 4,420,395 | 12/1983 | Tanihara et al. | 530/415 X |
| 4,528,198 | 7/1985 | Mizerak et al. | 426/16 |
| 4,595,578 | 6/1986 | Cohen et al. | 423/338 |
| 4,636,394 | 1/1987 | Hsu | 426/330.4 |
| 4,650,762 | 3/1987 | Boross et al. | 435/180 |
| 4,677,192 | 6/1987 | Obermeier et al. | 530/305 |
| 4,684,530 | 8/1987 | Welsh et al. | 426/330.5 |
| 4,929,560 | 5/1990 | Edmunds et al. | 435/226 |
| 4,952,322 | 8/1990 | Sugiyama et al. | 210/679 |
| 5,086,167 | 2/1992 | Awad, Jr. | 530/412 |

FOREIGN PATENT DOCUMENTS

| | | |
|---|---|---|
| 1178222 | 11/1984 | Canada . |
| 0235352 | 9/1987 | European Pat. Off. . |
| 0287232 | 10/1988 | European Pat. Off. . |
| 1215928 | 12/1970 | United Kingdom . |

OTHER PUBLICATIONS

Berg, Kenneth "New Chillproofing Agent", *Brewers Digest*, Nov. 1989, pp. 36–37.

Fernyhough et al. "Customized Silicas-A Science for the Future", *MBAA Technical Quarterly*, vol. 27, pp. 94–102, 1990.

*Primary Examiner*—Michael G. Wityshyn
*Assistant Examiner*—C. Sayala
*Attorney, Agent, or Firm*—Quarles & Brady

[57] ABSTRACT

A method of removing a valuable protein from a complex solution and recovering the valuable protein in purified form consists of adding a silica gel sorbant having a pore size approximately the molecular size of the protein to a solution containing the protein, allowing the protein to be sorbed onto the sorbant, separating the sorbant from the solution and then recovering the protein from the sorbant.

16 Claims, No Drawings

PROTEIN PURIFICATION METHOD

FIELD OF THE INVENTION

The present invention relates to a method of protein purification. More particularly, it relates to a method by which valuable proteins in complex solutions, such as fermentation broths and milk, can be removed and recovered in a purified form.

BACKGROUND OF THE INVENTION

Advances in biotechnology have made it possible to take a gene sequence which is responsible for the expression of a valuable protein in one organism, such as the human gene for insulin, and introduce it into another organism which expresses the valuable protein, for example into a fermentation broth or milk. Unfortunately, it is usually very difficult and expensive to isolate the valuable protein from the other components of the expression system. Isolation and purification are main contributors to the cost of the products.

It is known in the brewing industry that certain insoluble substances, such as silica gels, silica hydrogels and silica cogels, are "sorbants" which absorb, adsorb or entrap proteins and as such are useful in removing undesirable proteins from beer. The proteins are removed from the beer quickly and inexpensively.

The Raible U.S. Pat. No. 3,436,225 discloses a process for removing undesirable proteins from beer with a combination of silica gel and aluminum silicate.

The Barby et al. U.S. Pat. No. 3,617,301 discloses a process for the treatment of beer to reduce its tendency to form haze on storage which comprises adding to the beer a silica hydrogel. The patent also discloses that various other insoluble sorbants, such as bentonite, active carbon, nylon, polyvinyl pyrrolidone, as well as, other silica containing compounds have been previously used for this purpose and that they are to a greater or lesser extent effective.

The Hau U.S. Pat. No. 4,636,394 discloses the use of a combination of two distinct amorphous silicas to remove chill haze precursor proteins from beer.

The Mizerak et al. U.S. Pat. No. 4,528,198 discloses the use of sorbants, including silica hydrogel, to selectively remove yeast lethal factors from malt extract.

The Welsh et al. U.S. Pat. No. 4,684,530 discloses a method of removing haze-forming proteins from wine using inorganic oxide-silica cogels. The patent also discloses the regeneration and recycling of the cogel.

None of the above described patents disclose any method by which a valuable protein is removed from a broth and recovered.

There is a need for a simple method of removing and recovering valuable proteins from complex solutions, such as fermentation broths and milk, and also a need for a method of determining which valuable proteins can be removed from such solutions by that method.

SUMMARY OF THE INVENTION

It is an object of the present invention to disclose a method of removing and recovering valuable proteins from complex solutions, such as fermentation broths and milk.

It is a further object to disclose a method of determining whether a valuable protein can be removed and recovered from a complex solution by the method of the present invention.

The method of the present invention comprises adding to a complex solution that contains a valuable protein, a safe and effective amount of a silica gel sorbant, such as a silica hydrogel, xerogel or cogel, intimately mixing the silica gel in the complex solution to permit the valuable protein to come into contact with and be sorbed to the silica gel, removing the silica gel with the valuable protein sorbed thereon from the solution, and then desorbing the valuable protein from the sorbant under conditions that minimize the desorption of other sorbed components.

A method of avoiding undue experimentation in determining whether a valuable protein in a complex solution can be removed and recovered by the method of the present invention comprises adding a silica gel sorbant which has a pore size approximating that of the valuable protein to be recovered to a complex solution containing the valuable protein, intimately mixing the sorbant in the solution, allowing the sorbant to remain in the solution for about 10 to 30 minutes so that the protein can be sorbed to the sorbant, then removing the sorbant and treating samples of the sorbant with eluents which can disrupt the various bonds which might exist between the protein and the sorbant. The spent eluents are collected and analyzed to see if they contain the valuable protein. If they do, the method can be used to remove and recover the valuable protein.

The above and other objects and advantages of the invention will be apparent to those skilled in the art from the description which follows:

PREFERRED EMBODIMENT OF THE INVENTION

In the preferred embodiment of the invention, the method of the present invention comprises adding to a complex solution containing a valuable protein a silica gel sorbant to sorb the valuable protein present in the solution, intimately mixing the silica gel sorbant in the solution and allowing said silica gel sorbant to remain in the solution for about 10 to 30 minutes until a recoverable amount of the valuable protein has been sorbed onto the silica gel sorbant, the silica gel sorbant is then separated from the solution by conventional means, such as filtration. The silica gel sorbant with the valuable protein sorbed thereto is then treated with an eluent which disrupts the bonds that exist between the valuable protein and the sorbant so that the valuable protein can be separated from the sorbant and recovered from the eluent.

Representative of the valuable proteins which can be removed from a complex solution, such as a fermentation broth or milk, by the practice of the present invention are the following:

(a) Proteins, such as Anti Freeze Proteins (AFP), human serum albumin, and Tissue-Type Plasminogen Activator (TPA);

(b) Peptide hormones, such as Insulin;

(c) Enzymes or similar proteins, such as chymosin and alpha-1-antitrypsin;

(d) Other valuable proteins and peptides that can be isolated from fermentation broths, biological fluids, such as milk and, or other liquids or extracts. Examples being growth hormones, and other valuable pharmaceuticals.

Representative of the silica gel sorbants which can be used in the practice of the present invention are the following:

(a) Silica hydrogel, preferably the product having a pore size of about 100 angstroms, such as Britesorb A 100, which is available from P. Q. Corporation, Conshohocken, Pa. The Britesorb A100 can be dried to obtain a sorbant that has a smaller pore size, e.g. 25 angstroms.

(b) Silica xerogels.

(c) Silica cogels, preferably that product available under the tradename DP4660 from P. Q. Corporation.

Generally speaking, the sorbant selected will have a pore size approximating the molecular dimensions of the protein to be removed. However, if the protein is elliptically shaped or cylindrical the sorbant selected might be one having a smaller pore size that will accommodate that shape molecule. The amount of the sorbant to be added normally will depend upon the protein to be sorbed and its concentration in the solution. The amount used will preferrably be in excess of that required to sorb all the desired protein. In general, the amount will be much greater than the amounts used in chillproofing beer i.e. substantially in excess of 1000 ppm.

The Cohen et al. U.S. Pat. No. 4,595,578 discloses a method of making stabilized silica gels useful as sorbants in the method of the present invention.

Representative of the eluents that can be used in the practice of the present invention are (a) a hydrophobic interaction bond disrupting eluent, e.g., an eluent containing an alcohol, such as ethanol and/or isopropanol (b) an ion exchange bond disrupting eluent, e.g. an eluent containing salts, buffering agents and/or EDTA, (c) a hydrogen bond disrupting eluent, e.g. containing urea.

As previously described, silica hydrogels, xerogels, and cogels have been widely used in the brewing industry as chillproofing agents for the selective removal of certain undesired haze-causing proteins from beer. As a result, theories regarding the protein sorption mechanisms for these so-called chillproofing agents have been developed in terms of protein removal from beer. These theories may be useful in understanding the mechanisms which may be involved in the removal and recovery of valuable proteins from complex solutions, such as fermentation broths.

Fernyhough and Ryder (Ref. 1) recently summarized what is commonly thought to be the two primary principles behind the silica gel chillproofing of beer: "effective colloidal stabilization of beer essentially resides in two basic principles, viz., 1. selective adsorption and removal of haze-forming proteins (or precursors or associated products with polyphenols) due to interaction with active adsorption sites, i.e. isolated surface silanol (SiOH) groups on the amorphous silica particle.

2. selective removal of such components by permeation based on the pore structure and pore diameter distribution. It is considered that the binding of protein to silica gel is analogous to the binding of haze-forming proteins to polymerized polyphenols, that is, via hydrogen bonding of protein carbonyl groups to hydroxyl groups on either the polyphenol catechol ring or on the silica gel surface."

Thus, the two basic mechanisms cited by Fernyhough and Ryder are hydrogen bonding of protein to the silica gel surface (on the particle exterior surface or on the interior pore surfaces) and size-exclusion based on the ability of the protein to enter the pores of the silica.

Hough and Lovell (Ref. 2) also described sorption and size-exclusion as the two primary mechanisms for beer protein removal in a seminal paper in 1979. However, Hough and Lovell did not describe sorption in terms of hydrogen bonding. In this respect, Fernyhough and Ryder expanded on the theoretical basis of sorption presented by Hough and Lovell.

We have previously examined in our laboratories how the protein-containing fractions sorbed to silica hydrogel that had been used to chillproof beer could be eluted. In our work the protein-containing fractions were eluted from the silica hydrogel sequentially with: (1) an eluent with ethanol, salt and the 4.2 pH of beer, (2) an eluent of 0.05M ammonium bicarbonate, and EDTA with a pH of 8, and (3) an eluent bicarbonate buffer containing 8M urea and EDTA with a pH of 8.

It is our belief that the ethanol-containing eluent gently washes the proteins from the pores and matrix of the hydrogel (size-exclusion based elution). Analyses of the eluted material indicated that the proteins had been selectively sorbed, albeit weakly, since the analytical profiles did not correspond to beer profiles.

Further elution using an eluent containing EDTA and having a pH of 8 provided evidence for ion-exchange based separation. The EDTA in the eluent also may have disrupted divalent cation interactions that may have directly or indirectly participated in sorption to the hydrogel. The composition of the material eluted using this eluent was different than that of the material desorbed with the ethanol-containing eluent.

The final eluent we employed contained 8M urea, an agent that appears to disrupt hydrogen bonding. The composition of the material eluted using the eluent was different than the materials desorbed with the previous two eluents.

The results we obtained with this sequential elution of hydrogel indicated that the sorption mechanism is more complex than that described in the literature and can include any one or combination of size-exclusion, ion-exchange, possibly divalent cation interactions, and hydrogen bonding.

The materials eluted from the silica hydrogel included surface-active materials, browning products and beer proteins. This suggests that the proteins might not be sorbed directly to the hydrogel matrix, but rather that surface-active fractions might sorb to the matrix and beer proteins might sorb to the surface-active fractions.

It also has been suggested by others that polyphenols might sorb to silica hydrogels and proteins might sorb to the polyphenols. This idea is similar to the idea of surface-active components sorbing to silica hydrogels.

Other possible protein-hydrogel interaction modes which might be involved include hydrogen bonding, hydrophilic and hydrophobic interaction, van der Waals, and ionic interactions. In addition, the cogels, such as aluminosilicates or magnesium silicates, that contain metal ions are more ionic in character.

We also have observed that at the level of usage of less than 1000 ppm not all beer proteins are sorbed to silica hydrogels. In fact, the percent of protein sorption is not detectable by comparing beer total nitrogen values before and after chillproofing. Two beer protein fractions that are not sorbed to silica hydrogels are the beer protein fractions responsible for foam and small amounts of the yeast proteases that are found in the beer after fermentation.

In a model experiment employing proteins of defined molecular weight dissolved in a buffer, entrapment appeared to be a mechanism of protein sorption to silica hydrogel, silica cogel, and silica xerogel. Proteins of higher molecular weight were more efficiently sorbed than proteins of lower molecular weight. Lower molecular weight proteins appeared to be less firmly entrapped in the pores of the gel. The proteins examined were aldolase (MW 158,000), bovine serum albumin (MW 67,000), ovalbumin (MW 45,000), chymotrypsinogen A (MW 25,000) and ribonuclease A (MW 13,700).

All of these proteins were small enough to enter the pores of the gels. Protein of higher molecular weights would have been excluded from the pores of the gel (100 Angstroms for the silica hydrogel) and would either not have been entrapped (sorbed) or would have been sorbed to the surface of the gel.

The entrapment conclusions only directly relate to sorption from a simple buffer containing a few well-defined proteins. Additional sorption mechanisms may occur from complex solutions, such as fermentation broths. No relationship was obvious between protein sorption and the protein parameters of isoelectric point or surface activity. Both of these properties could play a role if there are secondary sorptions or interactions associated with sorption from complex solutions.

In general, the proteins and peptides and other molecules that can be purified by the present invention have a molecular weight of about 1,000 to about 250,000 and the preferred sorbant is one having a pore size approximating that of the protein. However, the selection can be affected by the shape of the protein molecule e.g. a smaller pore size can be used with an elliptically shaped protein molecule.

A partial listing of peptides and proteins of the type that may be purified by the practice of the present invention and the pore size of the suggested silica gel sorbant appear in Table 1.

TABLE 1

| Protein | M.W. | Suggested Silica Gel Pore Diameter (Angstroms) |
| --- | --- | --- |
| Human Epidermal Growth Factor | 6,000 | 25-50 |
| Methionyl Human Growth Hormone | 22,000 | 50 |
| Tissue Plasminogen Activating Factor | 64,000 | 100 |
| Human Gamma Interferon | 20,000-25,000 | 50 |
| Human Interleukin 2 | 15,000 | 50 |
| Tumor Necrosis Factor | 17,000 | 50 |
| Streptokinase | 47,400 | 100 |
| Invertase | 270,000 | 200 |
| Bovine Lysozyme | 14,400 | 50 |
| Human Serum Albumin | 69,000 | 100 |
| Human Lysozyme | 15,000 | 50 |
| Superoxide Dismutase | 32,600 | 50 |
| Alcohol Oxidase | 148,000 | 200 |

Experimental Work

We have shown in our laboratory that a variety of valuable proteins can be removed from complex solutions and recovered in purified form by a relatively simple method employing silica gel sorbants.

In our laboratory, we have shown that a recombinant form of a protein present in the body fluids of arctic fish which prevents them from freezing, i.e., Anti-Freeze Protein (AFP), can be sorbed from broths and other solutions onto either DP4660 (a silica cogel containing magnesium) or Britesorb A100 (a silica hydrogel) and selectively desorbed in purified form. Sorption to DP4660 was from either an ultrafiltration concentrate or from the original fermentation broth. Background materials were present in both broth and ultrafiltration concentrate that may influence sorption to, and desorption from, the silica gel.

Desorption of the AFP from the cogel DP4660 was achieved with a 50% v/v ethanol eluent, but desorption from the hydrogel Britesorb A100 was achieved with an eluent containing Tris- buffer, pH 8. This is evidence that the sorption methods of the two silica gels may be different. The ability to elute with the ethanol containing eluent indicates that the AFP sorption mechanism with DP4660 is probably due to a hydrophobic interaction. Whereas, elution of the AFP from Britesorb A100 with an eluent that changes the pH is more indicative of an ion-exchange interaction. It is interesting that hydrophobic interaction was indicated for the cogel and ion-exchange interaction for the hydrogel. Some of each type of interaction is probably partially responsible for sorption of AFP with both gels.

In another experiment chymosin, a valuable enzyme, was sorbed from an acetate buffer with silica xerogel. Desorption from the xerogel was with an acetate buffer (pH 5.6) eluent containing 25% isopropanol, again indicating that the sorption of chymosin to the xerogel was by a hydrophobic interaction. Sorption and desorption conditions from a fermentation broth could be different because of the influence of background material in the fermentation broth that could also sorb to the silica gel.

In still another experiment, insulin, in 0.25M acetic acid, was sorbed to the silica cogel DP4660. Desorption was achieved by using an eluent having a pH of 8 followed by further desorption with an eluent containing urea, a hydrogen-bond breaker. Evidence suggests that both ion-exchange and hydrogen-bonding may play a role in the sorption of insulin to the cogel DP4660.

It is possible that sorption and desorption conditions from a complex solution, such as a fermentation broth, could be different because of the influence of background material in the complex solution that would also sorb to the silica gel.

To demonstrate the usefulness of the method of the present invention in removing a valuable protein from milk still another experiment was conducted. In this experiment, AFP was mixed with cow's milk to yield a mixture which might be similar to the milk from a transgenic cow producing AFP. The AFP was effectively separated from the casein, whey milk proteins and cream with the silica cogel DP4660. The micellar forms of casein and whey were probably excluded from the cogel pores. The AFP was desorbed from the DP4660 with 50% ethanol.

The examples cited above suggest that there probably is no single simple mechanism that is responsible for the sorption of proteins to silica hydrogels, xerogels and cogels. Hydrogen bonding, size-exclusion, hydrophobic and hydrophilic interaction, and ionic and van der Waals interactions all probably play a role. Additionally, the sorption may be influenced by other components in the medium.

Additional experiments were done with various proteins of known molecular weight and isoelectric points in a well-defined buffer system.

Table 2 lists the protein standards (Pharmacia, Piscataway, N.J., Cat. #17-0441-01 and 17-0442-01) used for the analyses. The molecular weights were provided by the manufacturer. The isoelectric points (pI) were taken from tables published by Righetti (Ref. 3, 4 except for ovalbumin which was from Principles of Biochemistry (Ref. 5).

TABLE 1

| Protein | M.W. | Suggested Silica Gel Pore Diameter (Angstroms) |
|---|---|---|
| Human Epidermal Growth Factor | 6,000 | 25-50 |
| Methionyl Human Growth Hormone | 22,000 | 50 |
| Tissue Plasminogen Activating Factor | 64,000 | 100 |
| Human Gamma Interferon | 20,000-25,000 | 50 |
| Human Interleukin 2 | 15,000 | 50 |
| Tumor Necrosis Factor | 17,000 | 50 |
| Streptokinase | 47,400 | 100 |
| Invertase | 270,000 | 200 |
| Bovine Lysozyme | 14,400 | 50 |
| Human Serum Albumin | 69,000 | 100 |
| Human Lysozyme | 15,000 | 50 |
| Superoxide Dismutase | 32,600 | 50 |
| Alcohol Oxidase | 148,000 | 200 |

Size-exclusion (SE)-HPLC was performed with a TSK-G20000SW column (7.5 mm×60 cm, Beckman Altex, Fullerton, Calif., CAT. #233409). The mobile phase was pumped at 0.9 mL/min.

The mobile phase was pH 5 citrate-phosphate buffer prepared according to a formulation in Methods in Enzymology (Ref. 6), and 0.17M sodium chloride.

The protein standards were individually dissolved in 1 mL aliquots of mobile phase buffer to a concentration of approximately 1 mg/mL. For experiments, aliquots of the protein solutions were mixed. Aldolase, ovalbumin and ribonuclease A were used as a group, and bovine serum albumin and chymotrypsinogen A were used as a second group. Standard curves were prepared for each of the proteins (injected as groups) in the range of approximately 5-15 µg. The amount of aldolase injected was in the range of 11-33 µg because of lower 280 nm absorptivity. The standard mixture was also analyzed at the start of each day that sorption studies were performed to determine an HPLC response factor.

Silica gel sorption experiments were performed in 1.5 mL Eppendorf centrifuge tubes. Silica gel was weighted into a tube (0.6 mg to 400 mg). Buffer (less than 1 mL) was added and the tube was mixed on a vortex mixer to wet and disperse the silica gel. Protein solutions (approximately 150 µg each) were then added, increasing the volume to 1 mL. The tubes were placed on a Labquake (Lab Industries, Berkeley, Calif.) rocking shaker for 20 min. The tubes were then centrifuges for 5 min (Brinkman Eppendorf, Westbury, N.Y. Model 5415, 14,000×g). The supernatent was separated, recentrifuged for 2 min and analyzed by HPLC (100 µL injections).

The experimental results are summarized in Table 3.

TABLE 3

| Protein/silica hydrogel | | 0.01 g | 0.1 g | 0.4 g | | |
|---|---|---|---|---|---|---|
| Aldolase | | 18% sorb | sorb | sorb | | |
| Bovine Serum Albumin | | 25% sorb | sorb | sorb | | |
| Ovalbumin | | 50% sorb | sorb | sorb | | |
| Chymotrypsinogen A | | 5% sorb | 40% sorb | 70% sorb | | |
| Ribonuclease A | | 14% sorb | 70% sorb | 80% sorb | | |
| Protein/silica cogel | 0.0008 g | 0.0014 g | 0.005 g | 0.01 g | 0.2 g | |
| Aldolase | 10% sorb | 5% sorb | sorb | sorb | sorb | |
| Bovine Serum Albumin | 21% sorb | 42% sorb | sorb | sorb | sorb | |
| Ovalbumin | 24% sorb | 37% sorb | 81% sorb | sorb | sorb | |
| Chymotrypsinogen A | 31% sorb | 55% sorb | sorb | sorb | sorb | |
| Ribonuclease A | 22% sorb | 32% sorb | 81% sorb | sorb | sorb | |
| Protein/silica xerogel | 0.0006 g | 0.001 g | 0.01 g | 0.2 g | | |
| Aldolase | 16% sorb | 35% sorb | sorb | sorb | | |
| Bovine Serum Albumin | 36% sorb | 72% sorb | sorb | sorb | | |
| Ovalbumin | 38% sorb | 63% sorb | sorb | sorb | | |
| Chymotrypsinogen A | 49% sorb | 79% sorb | sorb | sorb | | |
| Ribonuclease A | 14% sorb | 24% sorb | 88% sorb | sorb | | |

The results presented in Table 3 indicate that the proteins examined required higher levels of the silica hydrogen for complete sorption than of the cogel or the xerogel.

The results also indicate that the higher molecular weight proteins sorb more strongly to these sorbants than the lower molecular weight proteins, with ribonuclease A being sorbed the least. The current results indicate that the higher molecular weight proteins enter the gel pores and are trapped, but lower molecular weight proteins may enter and then leave the pores.

The pore sizes for the silica hydrogel and xerogel are approximately 100 Angstroms each. Proteins for molecular diameters of up to approximately 80 Angstroms (MW 150,000; assuming a globular structure) can be separated by Sephadex G100 (Ref. 7 and 8). Making similar assumptions, proteins of up to a similar molecular weight could be entrapped by the hydrogel or xerogel.

The ovalbumin results for sorption to the silica cogel do not fit the pattern of protein entrapment as well as the other proteins and silica hydrogels, but the cogel apparently also contains magnesium.

No relationship is obvious between protein sorption and the protein properties of isoelectric point or surface activity which were also analyzed. Both of these properties could play a role if there are secondary sorptions and interactions associated with sorption from complex solutions. The results summarized in Table 3 directly relate to sorption from a simple buffer containing a few well-defined proteins.

Substantially higher levels of the silica cogel DP4660 need to be used to quantitatively isolate antifreeze protein from fermentation broths than are used to chillproof beer. As the level of antifreeze protein in the broth increases, the amount of DP4660 used to remove it also has to be increased. Large amounts of DP4660 may also be necessary because of the low molecular weight of the protein (MW<5,000). Some browning products are coeluted with the protein and need to be separated by a second step in the isolation procedure.

The results of the experiments indicate that protein entrapment appears to be the major mechanism of protein sorption to silica hydrogel, silica cogel, and silica xerogel. Proteins of higher molecular weight appear to be more efficiently sorbed than proteins of lower molecular weight.

The entrapment conclusions only directly relate to sorption from a simple buffer containing a few well-defined proteins. Additional sorption mechanisms may occur from complex solutions.

The complexity of the sorption mechanisms presents an opportunity for selective desorption, as well as a challenge for understanding the mechanism. Many, if not most, of the components in a complex solution, such as a fermentation broth or milk, will not sorb to silica hydrogels, xerogels or cogels. The sorption of other components will be influenced by the composition of the complex solution. Therefore, it is important to have a method such as that previously described for quickly determining the likelihood that a given valuable protein can be removed from a given solution and subsequently recovered in purified form.

The methods of the present invention make it possible to recover sorbed components of interest under conditions that are selective enough that most co-sorbed components would not be desorbed. However, even in cases where co-elution cannot be avoided, the valuable protein, or other component of interest can be quickly and inexpensively concentrated and purified to a degree that is difficult to achieve using other technologies. As a result, further purification will have been simplified by use of the method of the present invention.

It will be apparent to those skilled in the art that a number of modifications and changes may be made without departing from the spirit and scope of the present invention. As previously stated the terms "sorb" and "sorption" as used herein are intended to describe and include "absorb," "adsorb," "absorption" and "adsorption," as well as, "entrapment" and any other mechanisms by which the protein is bound to the sorbant. In addition, the term "protein" is intended to include other components of interest such as peptides, glycoproteins, and other molecules that can be sorbed and recovered by the practice of the method of the present invention. Therefore, it is intended that the invention not be limited except by the claims.

References

1. R. Fernyhough and D. S. Ryder, "Customized Silicas - A Science for the Future", MBAA Technical Quarterly, 27, p. 94–102 (1990).
J. S. Hough and A. L. Lovell, "Recent Developments in Silica Hydrogels for the Treatment and Processing of Beers", MBAA Technical Quarterly, 16, p. 90–100 (1979).
3. P. G. Righetti and T. Caravaggio, "Isoelectric Points and Molecular Weights of Proteins. A Table", J. Chromatography, 127, 1–28, 1976.
4 P. G. Righetti and G. Tudor, "Isoelectric Points and Molecular Weights of Proteins. A New Table", J. Chromatography, 220, 115–194, 1981.
5. A. White, P. Handler, and E. L. Smith, Principles of Biochemistry, Fourth Edition, McGraw-Hill, New York, N.Y., 1968.
6. Methods in Enzymology, Vol. I, page 141, S. P. Colowick and N. O. Kaplin, ed., Academic Press, New York, N.Y. 1955.
7. The Proteins, Third Edition, Vol. I, page 50, H. Neurath and R. L. Hill, ed., Academic Press, New York, N.Y., 1975.
8. Sephadex - Gel Filtration in Theory and Practice, Pharmacia, Uppsala Sweden.

We claim:

1. A method of removing a protein from a solution containing that protein, said method comprising adding to a solution containing the protein an effective amount of a sorbant consisting essentially of a member selected from the group consisting of a silica hydrogen, a silica cogel and a silica xerogel, to sorb at least some of the protein, intimately distributing the sorbant through the solution and permitting the sorbant to remain in the solution until the protein has been sorbed thereon, then removing from the solution the sorbant with protein sorbed thereon and treating said sorbant with an eluent which will disrupt bonds between the sorbant and the protein and permit the protein to be separated from the sorbant and recovered.

2. A method of claim 1 in which the protein is antifreeze protein.

3. A method of claim 1 in which the protein is chymosin.

4. A method of claim 1 in which the protein is insulin.

5. A method of claim 1 in which the sorbant is a silica hydrogel.

6. A method of claim 1 in which the sorbant is a silica xerogel.

7. A method of claim 1 in which the sorbant is a silica cogel.

8. A method of claim 1 in which the eluent is a hydrophobic solvent.

9. A method of claim 1 in which the eluent is a solvent that disrupts hydrogen bonds.

10. A method of claim 1 in which the eluent is a solvent that disrupts ion exchange bonds.

11. A method of identifying whether a specific protein can be effectively removed from a specific solution containing said protein by treatment with a sorbant consisting essentially of a member selected from the group consisting of a silica hydrogel, a silica cogel and a silica zerogel, said method comprising adding an effective amount of the sorbant to a sample of the solution containing the valuable protein to sorb the protein, intimately mixing the sorbant with the solution, allowing the sorbant to remain in the solution long enough for the protein to become sorbed thereon, then removing the sorbant from the solution and treating the sorbant with different eluents to see which of the eluents disrupt the bonds between the protein and the sorbant so that the protein can be separated and recovered.

12. A method of removing a protein having a molecular weight of about 1,000 to 250,000 from an aqueous preparation containing that protein, said method comprising adding to the preparation containing said protein an effective amount of a silica sorbant selected from the group consisting of a silica hydrogel, a silica cogel and a silica xerogel to sorb at least some of the valuable protein, intimately distributing the sorbant through the preparation and permitting the sorbant to remain in the preparation until said protein has been sorbed thereon, then removing from the preparation the sorbant with said protein sorbed thereon, and treating said sorbant with an eluent which will disrupt bonds between the sorbant and said protein and permit said protein to be separated and recovered.

13. A method of removing antifreeze protein from a solution containing antifreeze protein, said method comprising adding to an aqueous preparation containing antifreeze protein an effective amount of a silica sorbant selected from the group consisting of a silica cogel and a silica hydrogel to sorb at least some of the antifreeze protein, intimately distributing the sorbant through the solution and permitting the sorbant to remain in the preparation until the antifreeze protein has been sorbed thereon, then removing from the preparation the sorbant with antifreeze protein sorbed thereon, and treating said sorbant with an eluent which will disrupt bonds between the sorbant and the antifreeze protein and permit the antifreeze protein to be separated and recovered.

14. A method of claim 13 in which the silica sorbant is a silica cogel containing magnesium and the eluent is an aqueous ethanol solution.

15. A method of claim 13 in which the silica sorbant is a silica hydrogel and the eluent contains Tris-buffer, pH 8.

16. A method of removing a protein selected from the group consisting of antifreeze protein, insulin, chymosin, aldolase, ovalbumin, chymotrypsinogen A, ribonuclease A, human epidermal growth factor, methionyl human growth hormone, tissue plasminogen activating factor, human gamma interferon, human interleukin 2, tumor necrosis factor, streptokinase, invertase, bovine lysozyme, human serum albumin, human lysozyme, superoxide dismutase and alcohol oxidase from an aqueous preparation containing said protein, said method comprising adding to the preparation containing said protein an effective amount of a silica sorbant selected from the group consisting of silica hydrogels, silica cogels and silica xerogels to sorb at least some of said protein, intimately distributing the sorbant through the preparation and permitting the sorbant to remain in the preparation until said protein has been sorbed thereon, then removing from the preparation the sorbant with said protein sorbed thereon and treating said sorbant with an eluent which will disrupt bonds between the sorbant and said protein and permit said protein to be separated and recovered.

* * * * *

UNITED STATES PATENT AND TRADEMARK OFFICE
CERTIFICATE OF CORRECTION

PATENT NO. : 5,278,284
DATED : January 11, 1994
INVENTOR(S) : Lusk, et al.

It is certified that error appears in the above-identified patent and that said Letters Patent is hereby corrected as shown below:

Column 1, line 40          "Hau" should read --Hsu--

Column 7  lines 5 to 22    The complete Table 1 should be deleted and the following inserted

Table 2

| | | |
|---|---|---|
| Aldolase | MW 158,000 | pI 8.9 (Human) |
| Bovine Serum Albumin | MW 67,000 | pI 4.98, 5.07, 5.18 (Ox) |
| Ovalbumin | MW 43,000 | pI 4.6 |
| Chymotrypsinogen A | MW 25,000 | pI 8.8, 9.2, 9.6 (Beef) |
| Ribonuclease A | MW 13,700 | pI 8.7, 8.8 (Guinea Pig) |

Column 7, line 25          "TSKG 20000SW" should be --TSKG 2000SW--

Column 9, line 68          "hydrogen" should be --hydrogel--

Column 10, line 32         "zerogel" should be --xerogel--

Signed and Sealed this

Twenty-third Day of August, 1994

Attest:

BRUCE LEHMAN

Attesting Officer    Commissioner of Patents and Trademarks